(12) United States Patent
Epstein et al.

(10) Patent No.: US 7,960,102 B2
(45) Date of Patent: Jun. 14, 2011

(54) REGULATED APTAMER THERAPEUTICS

(75) Inventors: David Epstein, Belmont, MA (US); Charles Wilson, Concord, MA (US); John L. Diener, Cambridge, MA (US)

(73) Assignee: Archemix Corp., Cambridge, MA (US)

( * ) Notice: Subject to any disclaimer, the term of this patent is extended or adjusted under 35 U.S.C. 154(b) by 431 days.

(21) Appl. No.: 11/291,610

(22) Filed: Nov. 30, 2005

(65) Prior Publication Data

US 2006/0084109 A1 Apr. 20, 2006

Related U.S. Application Data

(63) Continuation of application No. 10/627,543, filed on Jul. 25, 2003, now abandoned.

(60) Provisional application No. 60/398,863, filed on Jul. 25, 2002, provisional application No. 60/398,846, filed on Jul. 25, 2002.

(51) Int. Cl.
*A61K 48/00* (2006.01)

(52) U.S. Cl. ........ 435/6; 325/375; 536/24.5; 536/24.31; 536/24.1

(58) Field of Classification Search ........................ None
See application file for complete search history.

(56) References Cited

U.S. PATENT DOCUMENTS

| | | | |
|---|---|---|---|
| 3,710,795 A | 1/1973 | Higuchi et al. | |
| 3,755,295 A | 8/1973 | Verheyden et al. | |
| 4,683,195 A | 7/1987 | Mullis | |
| 4,935,363 A | 6/1990 | Brown et al. | |
| 4,959,309 A | 9/1990 | Dattagupta et al. | |
| 5,070,010 A | 12/1991 | Hsu | |
| 5,118,672 A | 6/1992 | Schinazi et al. | |
| 5,143,854 A | 9/1992 | Pirrung et al. | |
| 5,262,564 A | 11/1993 | Kun et al. | |
| 5,270,163 A | 12/1993 | Gold et al. | |
| 5,338,671 A | 8/1994 | Scalice et al. | |
| 5,443,791 A | 8/1995 | Cathcart et al. | |
| 5,445,934 A | 8/1995 | Fodor et al. | |
| 5,459,015 A | 10/1995 | Janjic et al. | |
| 5,474,911 A | 12/1995 | Pontius | |
| 5,475,096 A | 12/1995 | Gold et al. | |
| 5,476,766 A | 12/1995 | Gold et al. | |
| 5,496,938 A | 3/1996 | Gold et al. | |
| 5,503,978 A | 4/1996 | Schneider et al. | |
| 5,567,588 A | 10/1996 | Gold et al. | |
| 5,580,737 A * | 12/1996 | Polisky et al. ..................... | 435/6 |
| 5,589,332 A | 12/1996 | Shih et al. | |
| 5,605,662 A | 2/1997 | Heller et al. | |
| 5,635,615 A | 6/1997 | Allen et al. | |
| 5,637,459 A | 6/1997 | Burke et al. | |
| 5,648,214 A | 7/1997 | Nieuwlandt et al. | |
| 5,654,151 A | 8/1997 | Allen et al. | |
| 5,660,985 A | 8/1997 | Pieken et al. | |
| 5,672,695 A | 9/1997 | Eckstein et al. | |
| 5,683,867 A | 11/1997 | Biesecker et al. | |
| 5,698,687 A | 12/1997 | Eckstein et al. | |
| 5,705,337 A | 1/1998 | Gold et al. | |
| 5,707,796 A | 1/1998 | Gold et al. | |
| 5,723,323 A | 3/1998 | Kauffman et al. | |
| 5,741,679 A | 4/1998 | George et al. | |
| 5,763,173 A | 6/1998 | Gold et al. | |
| 5,763,177 A | 6/1998 | Gold et al. | |
| 5,789,157 A | 8/1998 | Jensen et al. | |
| 5,817,635 A | 10/1998 | Eckstein et al. | |
| 5,834,186 A | 11/1998 | George et al. | |
| 5,859,228 A | 1/1999 | Janjic et al. | |
| 5,958,691 A | 9/1999 | Pieken et al. | |
| 5,998,142 A | 12/1999 | Gold et al. | |
| 6,001,067 A | 12/1999 | Shults et al. | |
| 6,011,020 A | 1/2000 | Gold et al. | |
| 6,013,443 A | 1/2000 | Heilig et al. | |
| 6,020,130 A | 2/2000 | Gold et al. | |
| 6,051,698 A | 4/2000 | Janjic et al. | |
| 6,083,696 A | 7/2000 | Biesecker et al. | |
| 6,229,002 B1 * | 5/2001 | Janjic et al. ..................... | 536/23.1 |
| 6,287,765 B1 | 9/2001 | Cubicciotti ..................... | 435/6 |
| 6,399,302 B1 | 6/2002 | Lannigan et al. ..................... | 435/6 |
| 6,465,189 B1 | 10/2002 | Biesecker et al. | |
| 6,630,306 B1 | 10/2003 | Breaker | |
| 6,670,132 B2 * | 12/2003 | Janjic et al. ..................... | 435/6 |
| 2003/0104520 A1 | 6/2003 | Ellington et al. | |
| 2003/0219422 A1 * | 11/2003 | Frauendorf et al. ....... | 424/93.21 |
| 2005/0176017 A1 | 8/2005 | Breaker | |

FOREIGN PATENT DOCUMENTS

| | | |
|---|---|---|
| EP | 0 592 035 B1 | 1/1996 |
| GB | 2 183 661 A | 6/1987 |
| WO | WO 89/06694 | 7/1989 |
| WO | WO 91/14436 | 10/1991 |
| WO | WO 91/19813 | 12/1991 |
| WO | WO 92/05285 | 4/1992 |
| WO | WO 92/07065 | 4/1992 |
| WO | WO 92/14842 | 9/1992 |

(Continued)

OTHER PUBLICATIONS

Burke et al., "Recombination, RNA evolution, and bifunctional RNA molecules isolated through Chimeric SELEX", *RNA*, 4:1165-1175 (1998).
Japanese Patent Application No. 2001-223818 (Japanese Laid-Open Publication No. 2003-033186 (2003).
Nippon Kagakkai Koen Yokoshu, Preprints of the Conference of the Chemical Society of Japan, 81(2):955, English abstract only, Abstract 2F6-12 (2002).
Nippon Kagakkai Koen Yokoshu, Preprints of the Conference of the Chemical Society of Japan, 79(2):950, English abstract only, Abstract 1F6 42 (2001).

(Continued)

*Primary Examiner* — Kimberly Chong
(74) *Attorney, Agent, or Firm* — Mintz Levin Cohn Ferris Glovsky and Popeo, P.C.; Ivor R. Elrifi

(57) ABSTRACT

Materials and methods of use thereof are presented for the treatment of diabetes and other diseases. Therapeutic compositions including regulated aptamer therapeutic compositions with specificity to components of diabetes disease are presented with methods of administering these therapeutic compositions.

8 Claims, 2 Drawing Sheets

FOREIGN PATENT DOCUMENTS

| | | |
|---|---|---|
| WO | WO 92/14843 | 9/1992 |
| WO | WO 94/13791 | 6/1994 |
| WO | WO 94/13833 | 6/1994 |
| WO | WO 96/17086 | 6/1996 |
| WO | WO 96/21730 | 7/1996 |
| WO | WO 98/08974 | 3/1998 |
| WO | WO 98/18480 | 5/1998 |
| WO | WO 98/27104 | 6/1998 |
| WO | WO 99/16781 | 4/1999 |
| WO | WO 99/31276 | 6/1999 |
| WO | WO 00/24426 | 5/2000 |
| WO | WO 00/24931 | 5/2000 |
| WO | WO 00/26226 | 5/2000 |
| WO | WO 00/43534 | 7/2000 |
| WO | WO 00/70329 | 11/2000 |
| WO | WO 01/09158 | 2/2001 |
| WO | WO 01/66721 | 9/2001 |
| WO | WO 01/96541 A2 | 12/2001 |
| WO | WO 01/96559 A2 | 12/2001 |
| WO | WO 02/22882 | 3/2002 |
| WO | WO 03/014375 | 2/2003 |

OTHER PUBLICATIONS

Seikagaku, *Biochemistry*, 73(8):946, English abstract only, Abstract 4P-012 (2001).
Wu et al., "An allosteric synthetic DNA", *Nucl. Acids Res.*, 27(6):1512-1516 (1999).
International Search Report for PCT/US03/23402, mailing date: Dec. 18, 2003.
Breaker (1997). Nat Biotech 15: 427-431.
Breaker (1997). Chem Rev 97: 371-390.
Breaker (1999). Intracellular Ribozyme Applications in Principles and Protocols, pp. 1-19; Horizon Press, Wymondham UK, Rossi and Couture, eds.
Breaker (2002). Curr Opin Biotech 13: 31-39.
Breaker (1997). Curr Opin Biotech 1:26-31.
Carmi, et al. (1996). Chem and Biol 3: 1039-1046.
Gold (2002). Nat. Biotech 20: 671-672.
Hamaguchi, et al. (2001). Anal Biochem 294: 126-131.
Hartig, et al. (2002). Nat Biotech 20: 717-722.
Jenne, et al. (2001). Nat Biotech 19: 56-61.
Koizumi, et al., (1999). Nat Struct Biol 6: 1062-1071.
Li and Breaker (1999). Curr Opin Struct Biol 9: 315-323.
Li and Breaker (1999). Proc Natl Acad Sci USA 96: 2746-2751.
Marshall and Ellington (1999). Nat Struct Bio 6 11: 992-994.
Robertson and Ellington (1999). Nat Biotech 17: 62-66.
Robertson & Ellington (2000) 3 Nucleic Acids Res 28: 1751-1759.
Robertson and Ellington (2001). Nat Biotech 19: 650-655.
Seetharaman, et al. (2001). Nat Biotech 19: 336-341.
Soukup and Breaker (1999). Proc Natl Acad Sci USA 96: 3584-3589.
Soukup and Breaker (1999). RNA 5: 1308-1325.
Soukup and Breaker (1999). Structure 7: 783-791.
Soukup and Breaker (1999). Tren Biotech 17: 469-476.
Soukup and Breaker (2000) in Ribo Biochem Biotech, Eaton Publ: 149-170, Krupp & Gaur, eds.
Tang and Breaker (1997). Chem Biol 4: 453-459.
Tang and Breaker (1998). Nuc Acids Res 26: 4214-4221.
Tang and Breaker (1997). RNA 3: 914-925.
Koizumi, et al., (1999). Nucleic Acids Symp Ser 42:275-276.
Potyrailo et al., (1998). Anal Chem, 70: 3419-3425.
Seiwert, et al., (2000). Chem Biol 7: 833-843.
Soukup, et al., (2000). Journal of Molecular Biology 298: 623-632.
Sassanfar & Szostak, (1993). Nature 363: 550-553.
Soukup et al., (2001). RNA 7: 524-536.
Sproat et al., (1990). Nuc Acids Res 19: 733-738.
Cotten et al., (1991). Nuc Acids Res 19: 2629-2635.
Hobbs et al., (1973). Biochemistry 12: 5138-5145.
Pagratis et al., (1997). Nat Biotechnol 15: 68-73.
Kraus et al., (1998). Journal of Immunology 160: 5209-5212.
Pieken et al., (1991). Science 253: 314-317.
Lin et al., (1994). Nucl Acids Res 22: 5529-5234.
Jellinek et al., (1995). Biochemistry 34: 11363-11372.
Soukup and Breaker, (1999). Structure Fold Des 7: 783-791.
Steele-Perkins and Roth, (1990). J. Biol. Chem. 265: 9458-9463.
Vuyisich and Beal, (2002). Chemistry and Biology 9: 907-913.
McCollum and Gould, (2001). Trends Cell Biol 11: 89-95.
Ambros, (2000). Curr. Opin. Genet. Dev. 10: 428-433.
Lee and Ambros, (2001). Science 294: 862-864.
Wilson and Szostak, (1999). Annu. Rev. Biochem. 66: 611-647.
Hermann and Patel, (2000). Science 287: 820-825.
Jenison, et al., (1994). Science 263: 1425-1429.
Soukup and Breaker, (1999). Proc Natl. Acad. Sci. 28: 3584-3589.
Robertson and Ellington, (2000). Nucleic Acids Res. 28: 1751-1759.
Piganeau et al., (2000). Angew Chem. Int. Ed. 39: 4369-4373.
Hartig et al., (2002). Nat. Biotechnol. 20: 717-722.
Koizumi et al., (1999). Nat. Struct. Biol. 6: 1062-1071.
Chestanga and Lindahl, (1979). Nucl Acids Res. 10: 3673-3684.
Boiteux et al., (1990). J. Biol. Chem. 265: 3916-3922.
David and Williams, (1998). Chem. Rev. 98: 1221-1261.
Tchou et al., (1991). Proc. Natl. Acad. Sci. USA 88: 340-348.
Moazed and Noller, (1987). Nature 327: 389-394.
Yoshizawa et al., (2002). Biochemistry 41: 6263-6270.
Carter et al., (2000). Nature 407: 340-348.
Wallis, et al., (1995). Chem. Biol. 2: 543-552.
Leipold, et al., (2000). Biochemistry 39: 14984-14992.
Zharkov et al., (1997). J. Biol. Chem. 5335-5342.
Mathews et al., (1999). J. Mol. Biol. 288: 911-940.
Famulok et al., (2001). Chem. Biol. 8: 931-939.
Ellington and Szostak, (1990). Nature 346: 818-822.
Hermann, (2000). Angew. Chem. Int. Ed. 39: 1890-1905.
Thomas et al., (1997). J. Biol. Chem. 272: 27980-27986.
Breaker (1996). Curr Opin Biotech 7: 442-448.
Andrake et al. *Proc. Natl. Acad. Sci. USA*, (1988) 85:7942-7946.
Araki et al. *Nucl. Acids Res.*, (1998) 26(14):3379-3384.
Aurup et al., *Biochem.*, (1992) 31:9636-9641.
Beaudry et al. *Science*, (1992) 257:635-641.
Belshaw et al. *Angew. Chem. Int. Ed. Engl.*, (1995) 34(19):2129-2132.
Bock et al. *Nature*, (1992) 355:564-566.
Breaker et al. *Chem. Biol.*, (1994) 1:223-229.
Carey et al. *Biochem.*, (1983) 22(11):2601-2610.
Chaires *J. Biol. Chem.*, (1986) 261(19):8899-8907.
Chen et al., *Biochem.*, (1977) 16(15):3310-3315.
Cohen et al. *Proc. Natl. Acad. Sci. USA.*, (1969) 63:458-464.
Davis et al. *Meth. Enzymol.*, (1996) vol. 267:302-314.
Dehouck et al. *Biology and Physiology of the Blood Brain Barrier*, Couraud and Scherman eds., (1996) Chapter 23, pp. 143-146.
Ellington et al. Abstracts of papers presented at the 1990 meeting on RNA Processing, Cold Spring Harbor Laboratory, Cold Spring Harbor, NY, (1990) pp. 84-85.
Epstein et al. "Archemix, Evolving Drug Discovery," Scientific presentation in Cambridge, MA., USA on Dec. 12, 2001.
Epstein et al. "Archemix, Evolving Drug Discovery," Scientific Presentation in La Jolla, CA., USA, on Jan. 4, 2002.
Epstein et al. "Enabling Drug Discovery Through the Power of Evolution," Scientific presentation in Berlin, CT., USA on Jun. 17, 2001.
Fitzwater et al. *Meth. Enzymol.*, (1996) 267:275-301.
Froehler et al. *Nucl. Acid Res.*, (1986) 14(13):5399-5407.
Froehler et al. *Tet. Lett.*, (1986) 27(46):5575-5578.
Frohman et al. *Proc. Natl. Acad. Sci. USA*, (1988) 85:8998-9002.
Gath et al. *Biology and Physiology of the Blood Brain Barrier*, Couraud and Scherman eds., (1996) Chapter 25, pp. 153-158.
Gold et al. *Annu. Rev. Biochem.*, (1995) 64:763-797.
Hirose et al., *Tet. Lett.*, (1978) 28:2449-2452.
Joyce et al. *Nucl. Acids Res.*, (1989) 17(2):711-722.
Joyce *Gene*, (1989) 82:83-87.
Kacian et al. *Proc. Natl. Acad. Sci. USA*, (1972) 69(10):3038-3042.
Kadonaga et al. *Proc. Natl. Acad. Sci. USA*, (1986) 83:5889-5893.
Kellogg et al. *BioTechniques*, (1994) 16(6):1134-1137.
Kinzler et al. *Nucl. Acids Res.*, (1989) 17(10):3645-3653.
Kinzler et al. *Mol. Cell. Biol.*, (1990) 10(2):634-642.
Kramer et al. *J. Mol. Biol.*, (1974) 89:719-736.
Kuruvilla et al. *Nature*, (2002) 416:653-657.
Leach et al. *J. Am. Chem. Soc.*, (1951) 73:2794-2797.
Lestienne et al. *Biochimie*, (1983) 65:49-52.
Levisohn et al. Proc. Natl. Acad. Sci. USA, (1968) 60:866-872.

Levisohn et al. *Proc. Natl. Acad. Sci. USA*, (1969) 63:805-811.
Ma et al. *Cell*, (1987) 51:113-119.
Maniatis et al. Molecular Cloning: a Laboratory Manual, Cold Spring Harbor, NY, (1982) p. 118.
Maniatis et al. *Science*, (1987) 236: 1237-1245.
Matthews et al. *Anal. Biochem.*, (1988) 169:1-25.
McKenna et al. *J. Med. Chem.*, (2002) 45:2173-2184.
Miele et al. *J. Mol. Biol.*, (1983) 171:281-295.
Milligan et al. *J. Med. Chem.*, (1993) 36(14):1923-1937.
Mills et al. *Science*, (1973) 180:916-927.
Mills et al. *Proc. Natl. Acad. Sci. USA*, (1967) 58:217-224.
Min et al. *Nucl. Acids Res.*, (1988) 16(11):5075-5087.
Muesing et al. *Nature*, (1985) 313:450-458.
Mullis et al. *CSHS Quant. Biol.*, LI 263-273 (1986).
Norman et al. *J. Am. Chem. Soc.*, (1996) 118(31):7430-7431.
Oliphant et al. *Meth. Enzymol*, (1987) 155:568-582.
Oliphant et al. *Nucl. Acids Res.*,16(15):7673-7683, 1988.
Oliphant et al. *Gene*, (1986) 44:177-183.
Oliphant et al. *Mol. Cell. Biol.*, (1989) 9:2944-2949.
Orgel *Proc. R. Soc. Lon. B*, (1979) 205:435-442.
Ou et al. *Science*, (1988) 239:295-297.
Padilla et al. *Nucl. Acids Res.*, (1999) 27(6):1561-1563.
Pease et al. *Proc. Natl. Acad. Sci.*, (1994) 91: 5022-5026.
Porta et al. *Biotechnol.*, (1995) 13(2):161-164.
Robertson et al. *Nature*, (1990) 344:467-468.
Romaniuk et al. *Biochem.*, (1987) 26(6):1563-1568.
Saffhill et al. *J. Mol. Biol.*, (1970) 51:531-539.
Sambrook et al. Molecular Cloning: A Laboratory Manual, Cold Spring Harbor, NY, (1989) Section 8.9-8.10.
Schena et al. *Proc. Natl. Acad. Sci. USA*, (1996) 93:10614-10619.
Sen *Chem. Biol.*, (2002) 9:851-855.
Shen et al. *J. Biol. Chem.*, (2001) 276(50):47311-47319.
Singleton et al. Dictionary of Microbiol. & Molec. Biol., Wiley & Sons, New York, NY, 2nd ed. p. 493, 1978.
Sood et al. *Nucl. Acid Res.*, (1977) 4(8):2757-2765.
Specht *Curr. Opin. Cell Biol.*, (2002) 14:155-159.
Szostak "A Structure and Activity of Ribozymes", Redesigning the Molecules of Life, (SA Benner ed.) Springer-Verlag Berline Heidelberg, pp. 87-113 (1988).
Talbot et al. *Nucl. Acids Res.*, (1990) 18(12):3521-3528.
Tanchou et al. *Aids Res. Hum. Retroviruses*, (1994) 10(8):983-993.
Thiesen et al. *Nucl. Acids Res.*, (1990) 18(11):3203-3209.
Tucker et al. *J. Chromatography B.*, (1999) 732:203-212.
Tuerk et al. *Science*, (1990) 249:505-510.
Tyagi et al. *Nat. Biotechnol.*, (1996) 14(3) 303-308.
Uhlenbeck et al. *J. Biomol. Struct. Dynamics*, (1983) 1:539-552.
Verdugo et al. *Med. Chem.*, (2001) 44:2683-2686.
Verheyden et al. *J. Org. Chem.*, (1971) 36(2):250-254.
Watson et al. Molecular Biology of the Gene, Benjamin/Cummings Publishing Co., Inc. California, (1987) pp. 267,295,323,361,394,396,397 and 405.
Wecker et al. *RNA*, (1996) 2:982:994.
Weintraub, Cold Springs Harbor Symp. Quant. Biol. (1973) 38:247-256.
Xu et al. *Proc. Natl. Acad. Sci. USA*, (1996) 93(15): 7475-7480.
Yang et al. *Biochem.*, (1992) 31:5005-5009.
Burke et al., *RNA*, (1998) 4:1165-1175.
Stojanovic et al., *J. Am. Chem. Soc.*, (2004) 126:9266-9270.
Wu et al., *Nuc. Acids Res.*, (1999) 27(5):1512-1516.
Database BIOSIS [Online] Biosciences Information Service, Philadelphia, PA, US; XP002429558 Database accession No. PREV200200547341; abstract Vuyisich et al., "Controlling protein activity with ligand-regulated RNA aptamers", *Chemistry & Biology* (2002) 9(8): 907-913; ISSN 1074-5521.
Jose et al., "Cooperative binding of effectors by an allosteric ribozyme", (2001) *Nucl. Acids Res.* 29(7): 1631-1637.
Wang et al., "A general approach for the use of oligonucleotide effectors to regulate the catalysis of RNA-cleaving ribozymes and DNAzymes", (2002) *Nucl. Acids Res.* 30(8): 1735-1742.
Supplemental European Search Report from European Patent Application No. 03771887.1, 2007.

* cited by examiner

Figure 1 –. *In vitro* aptamer selection process from pools of random sequence oligonucleotides

REGULATED APTAMER THERAPEUTICS

REFERENCE TO RELATED APPLICATIONS

This application is a continuation of U.S. patent application Ser. No. 10/627,543, filed Jul. 25, 2003 now abandoned, which claims priority to and is related to U.S. Provisional Application Ser. No. 60/398,863, filed Jul. 25, 2002; and U.S. Provisional Application Ser. No. 60/398,846, filed Jul. 25, 2002; each of which is herein incorporated by reference in its entirety.

FIELD OF THE INVENTION

The invention relates generally to the field of nucleic acids and more particularly to compositions and methods for treating diseases with regulated aptamer compositions of the present invention.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies (MAbs), are capable of specifically binding to selected targets and, through binding, block their targets' ability to function. Created by an in vitro selection process from pools of random sequence oligonucleotides (FIG. 1), aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

Aptamers have a number of desirable characteristics for use as therapeutics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process. In vitro selection allows the specificity and affinity of the aptamer to be tightly controlled and allows the generation of leads against both toxic and non-immunogenic targets.

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers (most likely because aptamers cannot be presented by T-cells via the MHC and the immune response is generally trained not to recognize nucleic acid fragments).

3) Administration. Whereas all currently approved antibody therapeutics are administered by intravenous infusion (typically over 2-4 hours), aptamers can be administered by subcutaneous injection. This difference is primarily due to the comparatively low solubility and thus large volumes necessary for most therapeutic MAbs. With good solubility (>150 mg/ml) and comparatively low molecular weight (aptamer: 10-50 KD; antibody: 150 KD), a weekly dose of aptamer may be delivered by injection in a volume of less than 0.5 ml. Aptamer bioavailability via subcutaneous administration is >80% in monkey studies (Tucker, 1999).

4) Scalability and cost. Aptamers are chemically synthesized and consequently can be readily scaled as needed to meet production demand. Whereas difficulties in scaling production are currently limiting the availability of some biologics (e.g., Ebrel, Remicade) and the capital cost of a large-scale protein production plant is enormous (e.g., $500 MM, Immunex), a single large-scale synthesizer can produce upwards of 100 kg oligonucleotide per year and requires a relatively modest initial investment (e.g., <$10 MM, Avecia). The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Aptamers are chemically robust. They are intrinsically adapted to regain activity following exposure to heat, denaturants, etc. and can be stored for extended periods (>1 yr) at room temperature as lyophilized powders. In contrast, antibodies must be stored refrigerated.

Diabetes Therapeutics. Diabetes is a disease involving abnormal regulation of glucose in the bloodstream. The insulin receptor (IR) is a surface receptor and is a tetramer of 2 alpha and 2 transmembrane beta chains linked by disulfide bonds. The insulin receptor, which is activated by insulin, is a tyrosine kinase receptor. Its activation leads to an increase in the storage of glucose with a concomitant decrease in hepatic glucose release to the circulation. The insulin receptor induces a cellular response by phosphorylating proteins on their tyrosine residues. The IR is known to phosphorylate several proteins in the cytoplasm, including insulin receptor substrates (IRSs) and Shc. Phosphatidylinositol 3-kinase (PKI3) is one signaling molecule that is activated by binding IRSs and is important in coupling the IR to glucose uptake. PKI3 mediates glucose uptake by the IR as well as a variety of other cellular responses by generating $PI(3,4)P_2$ and $PI(3,4,5)P_3$. $PI(3,4)P_2$ and $PI(3,4,5)P_3$ then function directly as second messengers to activate downstream signaling molecules by binding pleckstrin homology (PH) domains in these signaling molecules.

The major function of insulin is to counter the concerted action of a number of hyperglycemia-generating hormones and to maintain low blood glucose levels. Because there are numerous hyperglycemic hormones, untreated disorders associated with insulin generally lead to severe hyperglycemia and shortened life span. Insulin is synthesized as a pre-prohormone in the b cells of the islets of Langerhans. Its signal peptide is removed in the cisternae of the endoplasmic reticulum and it is packaged into secretory vesicles in the Golgi, folded to its native structure, and locked in this conformation by the formation of 2 disulfide bonds. Specific protease activity cleaves the center third of the molecule, which dissociates as C peptide, leaving the amino terminal B peptide disulfide bonded to the carboxy terminal A peptide. Insulin secretion from b cells is principally regulated by plasma glucose levels, but the precise mechanism by which the glucose signal is transduced remains unclear. One possibility is that the increased uptake of glucose by pancreatic b-cells leads to a concomitant increase in metabolism. The increase in metabolism leads to an elevation in the ATP/ADP ratio. This in turn leads to an inhibition of an ATP-sensitive $K^+$ channel. The net result is a depolarization of the cell leading to $Ca^{2+}$ influx and insulin secretion. Chronic increases in numerous other hormones—including growth hormone, placental lactogen, estrogens, and progestins—up-regulate insulin secretion, probably by increasing the preproinsulin mRNA and enzymes involved in processing the increased preprohormone. In contrast, epinephrine diminishes insulin secretion by a cAMP-coupled regulatory path. In addition, epinephrine counters the effect of insulin in liver and peripheral tissue, where it binds to b-adrenergic receptors, induces adenylate cycles activity, increases cAMP, and activates PKA activates PKA similarly to that of glucagon. The latter events induce glycogenolysis and gluconeogenesis, both of which are hyperglycemic and which thus counter insulin's effect on blood glucose levels. In addition, epinephrine influences glucose homeostasis through interaction with a-adrenergic receptors. Insulin secreted by the pancreas is directly infused via the portal vein to the liver, where it exerts profound metabolic effects. These effects are the response of the activation of the insulin receptor which belongs to the class of cell surface receptors that exhibit intrinsic tyrosine kinase activity. With respect to hepatic glucose homeostasis, the effects of insulin receptor activation are specific phosphorylation events that lead to an increase in the storage of glucose with a concomitant decrease in hepatic glucose release to the circulation.

In most other tissues insulin increases the number of plasma membrane glucose transporters, but in liver glucose uptake is dramatically increased because of increased activity of the enzymes glucokinase, phosphofructokinase-1 (PFK-1), and pyruvate kinase (PK), the key regulatory enzymes of glycolysis. The latter effects are induced by insulin-dependent activation of phosphodiesterase, with decreased PKA activity and diminished phosphorylation of pyruvate kinase and phosphofructokinase-2, PFK-2. Dephosphorylation of pyruvate kinase increases its' activity while dephosphorylation of PFK-2 renders it active as a kinase. The kinase activity of PFK-2 converts fructose-6-phosphate into fructose-2,6-bisphosphate (F2,6BP). F2,6BP is a potent allosteric activator of the rate limiting enzyme of glycolysis, PFK-1, and an inhibitor of the gluconeogenic enzyme, fructose-1,6-bisphosphatase. In addition, phophatases specific for the phosphorylated forms of the glycolytic enzymes increase in activity under the influence of insulin. All these events lead to conversion of the glycolytic enzymes to their active forms and consequently a significant increase in glycolysis. In addition, glucose-6-phosphatase activity is down-regulated. The net effect is an increase in the content of hepatocyte glucose and its phosphorylated derivatives, with diminished blood glucose. In addition to the latter events, diminished cAMP and elevated phosphatase activity combine to convert glycogen phosphorylase to its inactive form and glycogen synthase to its active form, with the result that not only is glucose funneled to glycolytic products, but glycogen content is increased as well.

Insulin therapy is the only treatment for Type 1 diabetic patients. Occasionally, Type 2 diabetic patients are also treated with insulin. Type 2 diabetic patients usually require larger doses of insulin to achieve the target blood glucose value. At present, two methods of insulin delivery are available in the USA; multiple daily insulin injections and an insulin pump. Nasal insulin therapy is currently undergoing clinical trials and is not yet approved by the FDA for general use. All insulins sold in the United States today are of U-100 strength, 100 units of insulin per cc of fluid. There are other dilutions in other countries. Dosing is at least three times a day with meals.

Insulin generates its intracellular effects by binding to a plasma membrane receptor, which is the same in all cells. The receptor is a disulfide-bonded glycoprotein. One function of insulin (aside from its role in signal transduction.) is to increase glucose transport in extrahepatic tissue is by increasing the number of glucose transport molecules in the plasma membrane. Glucose transporters are in a continuous state of turnover. Increases in the plasma membrane content of transporters stem from an increase in the rate of recruitment of new transporters into the plasma membrane, deriving from a special pool of preformed transporters localized in the cytoplasm. In addition to its role in regulating glucose metabolism, insulin stimulates lipogenesis, diminishes lipolysis, and increases amino acid transport into cells. Insulin also modulates transcription, altering the cell content of numerous mRNAs. It stimulates growth, DNA synthesis, and cell replication, effects that it holds in common with the IGFs and relaxin.

The most common method of insulin delivery is subcutaneous injection. Another method is an insulin pump. The biggest advantage of an insulin pump is greater flexibility in the timing of meals, the patient does not have to eat at a particular time as is the case with insulin injection therapy. Meals can be skipped without the fear of low blood sugar. The disadvantages of insulin pump delivery are the risk of skin infection at the needle site, insulin delivery can be halted due to mechanical problems which can result in severe hyperglycemia (high blood glucose) and even diabetic ketoacidosis (a life-threatening condition), and cosmetic problems.

Despite the benefits of insulin therapy to treat type 1 diabetes, there are difficulties with regulation of effective plasma levels of insulin therapeutics. There is therefore a need for a therapeutic that effectively regulates insulin therapeutics in vivo.

SUMMARY OF THE INVENTION

The present invention provides regulated aptamers that can be used, e.g., to treat certain diseases. More specifically, the present invention provides aptamers wherein binding of the aptamer to a second ligand is regulated, i.e., activated or suppressed, by binding to a first (or effector) ligand.

In one embodiment, the present invention provides therapeutic aptamers whose binding activity is controlled by a first ligand which serves, e.g., as a disease marker. The first ligand activates the binding activity of the therapeutic aptamer.

In one embodiment, the present invention provides therapeutic aptamers whose binding activity is controlled by a first ligand which serves, e.g., as a disease marker. The first ligand suppresses the binding activity of the therapeutic aptamer.

In one embodiment, the present invention provides therapeutic aptamers that bind to the insulin receptor (thus triggering glucose uptake by cells) only after binding glucose.

DETAILED DESCRIPTION OF THE INVENTION

Definitions
As defined herein, aptamers are nucleic acid ligands which have the property of binding specifically to a desired target compound or molecule or a nucleic acid target through non-Watson-Crick base pairing.

As defined herein a regulated aptamer is an aptamer whose binding (or other biological) activity is controlled allosterically by an effector ligand which serves, e.g., as a disease marker. The effector ligand can either activate or suppress the binding (or other biological) activity of the aptamer.

As defined herein, an agonist-aptamer is an aptamer that activates the activity of a target when it binds thereto.

As defined herein, an antagonist-aptamer is an aptamer which inactivates the activity of a target when it binds thereto.

Figure 1:
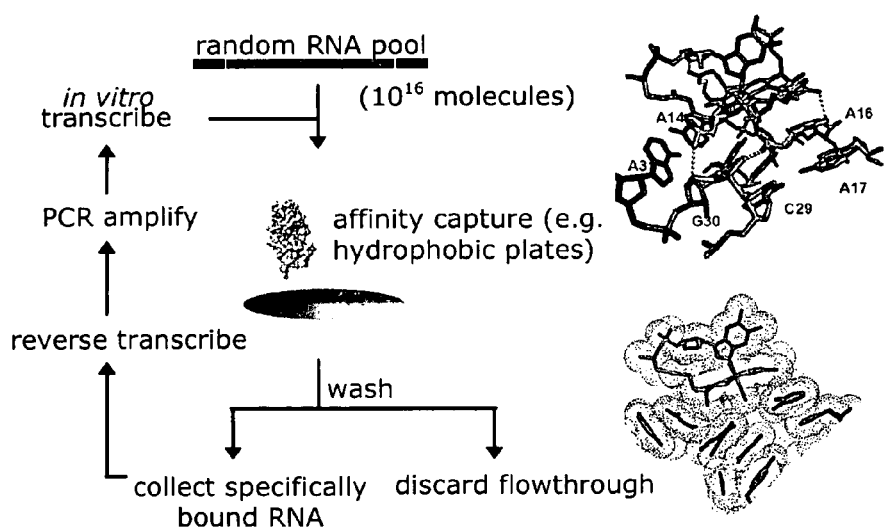
FIG. 1 shows a schematic of the SELEX method.

A suitable method for generating an aptamer to a target of interest is with the process entitled "Systematic Evolution of Ligands by EXponential Enrichment" ("SELEX™") depicted in FIG. 1. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

Systematic Evolution of Ligands by Exponential Enrichment, "SELEX™," is a method for making a nucleic acid ligand for any desired target, as described, e.g., in U.S. Pat. Nos. 5,475,096 and 5,270,163, and PCT/US91/04078, each of which is specifically incorporated herein by reference.

SELEX™ technology is based on the fact that nucleic acids have sufficient capacity for forming a variety of two- and three-dimensional structures and sufficient chemical versatility available within their monomers to act as ligands (i.e., form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

Within a nucleic acid mixture containing a large number of possible sequences and structures, there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20-50 nucleotides.

The basic SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes a SELEX™ based methods for selecting nucleic acid ligands containing photoreactive groups capable of binding and/or photocrosslinking to and/or photoinactivating a target molecule. U.S. Pat. No. 5,567,588 and U.S. application Ser. No. 08/792,075, filed Jan. 31, 1997, entitled "Flow Cell SELEX", describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target. Each of these patents and applications is specifically incorporated herein by reference.

SELEX™ can also be used to obtain nucleic acid ligands that bind to more than one site on the target molecule, and to nucleic acid ligands that include non-nucleic acid species that bind to specific sites on the target. SELEX™ provides means for isolating and identifying nucleic acid ligands which bind to any envisionable target, including large and small biomolecules including proteins (including both nucleic acid-binding proteins and proteins not known to bind nucleic acids as part of their biological function) cofactors and other small molecules. See U.S. Pat. No. 5,580,737 for a discussion of nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of a) preparing a candidate mixture of nucleic acids; b) contacting the candidate mixture with the target, wherein nucleic acids having an increased affinity to the target relative to the candidate mixture may be partitioned from the remainder of the candidate mixture; c) partitioning the increased affinity nucleic acids from the remainder of the candidate mixture; d) contacting the increased affinity nucleic acids with one or more non-target molecules such that nucleic acid ligands with specific affinity for the non-target molecule(s) are removed; and e) amplifying the nucleic acids with specific affinity to the target molecule to yield a mixture of nucleic acids enriched for nucleic acid sequences with a relatively higher affinity and specificity for binding to the target molecule.

For example, a heterogeneous population of oligonucleotide molecules comprising randomized sequences is generated and selected to identify a nucleic acid molecule having a binding affinity which is selective for a target molecule. (U.S. Pat. Nos. 5,475,096; 5,476,766; and 5,496,938) each of is incorporated herein by reference. In some examples, a population of 100% random oligonucleotides is screened. In others, each oligonucleotide in the population comprises a random sequence and at least one fixed sequence at its 5' and/or 3' end. The oligonucleotide can be RNA, DNA, or mixed RNA/DNA, and can include modified or nonnatural nucleotides or nucleotide analogs. (U.S. Pat. Nos. 5,958,691; 5,660,985; 5,958,691; 5,698,687; 5,817,635; and 5,672,695, PCT publication WO 92/07065).

The random sequence portion of the oligonucleotide is flanked by at least one fixed sequence which comprises a sequence shared by all the molecules of the oligonucleotide population. Fixed sequences include sequences such as hybridization sites for PCR primers, promoter sequences for RNA polymerases (e.g., T3, T4, T7, SP6, and the like), restriction sites, or homopolymeric sequences, such as poly A or poly T tracts, catalytic cores (described further below), sites for selective binding to affinity columns, and other sequences to facilitate cloning and/or sequencing of an oligonucleotide of interest.

In one embodiment, the random sequence portion of the oligonucleotide is about 15-70 (e.g., about 30-40) nucleotides in length and can comprise ribonucleotides and/or deoxyribonucleotides. Random oligonucleotides can be synthesized from phosphodiester-linked nucleotides using solid phase oligonucleotide synthesis techniques well known in the art (Froehler et al., Nucl. Acid Res. 14:5399-5467 (1986); Froehler et al., Tet. Lett. 27:5575-5578 (1986)). Oligonucleotides can also be synthesized using solution phase methods such as triester synthesis methods (Sood et al., Nucl. Acid Res. 4:2557 (1977); Hirose et al., Tet. Lett., 28:2449 (1978)). Typical syntheses carried out on automated DNA synthesis equipment yield $10^{15}$-$10^{17}$ molecules. Sufficiently large regions of random sequence in the sequence design increases the likelihood that each synthesized molecule is likely to represent a unique sequence.

To synthesize randomized sequences, mixtures of all four nucleotides are added at each nucleotide addition step during the synthesis process, allowing for random incorporation of nucleotides. In one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985, which describes oligonucleotides containing nucleotide derivatives chemically modified at the 5' and 2' positions of pyrimidines. U.S. Pat. No. 5,756,703 describes oligonucleotides containing various 2'-modified pyrimidines. U.S. Pat. No. 5,580,737 describes highly specific-nucleic acid ligands containing one or more nucleotides modified with 2'-amino (2'-$NH_2$), 2'-fluoro (2'-F), and/or 2'-O-methyl (2'-OMe) substituents.

The SELEX method encompasses combining selected oligonucleotides with other selected oligonucleotides and non-oligonucleotide functional units as described in U.S. Pat. No. 5,637,459 and U.S. Pat. No. 5,683,867. The SELEX method further encompasses combining selected nucleic acid ligands with lipophilic or non-immunogenic high molecular weight compounds in a diagnostic or therapeutic complex, as described in U.S. Pat. No. 6,011,020. VEGF nucleic acid ligands that are associated with a lipophilic compound, such as diacyl glycerol or dialkyl glycerol, in a diagnostic or therapeutic complex are described in U.S. Pat. No. 5,859,228.

VEGF nucleic acid ligands that are associated with a lipophilic compound, such as a glycerol lipid, or a non-immunogenic high molecular weight compound, such as polyalkylene glycol are further described in U.S. Pat. No. 6,051,698. VEGF nucleic acid ligands that are associated with a non-immunogenic, high molecular weight compound or a lipophilic compound are further described in PCT Publication No. WO 98/18480. These patents and applications allow the combination of a broad array of shapes and other properties, and the efficient amplification and replication properties, of oligonucleotides with the desirable properties of other molecules.

Each of the above references, which describe modifications of the basic SELEX procedure are specifically incorporated by reference in its entirety.

The identification of nucleic acid ligands to small, flexible peptides via the SELEX method has been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified. This reference is specifically incorporated by reference in its entirety.

To generate oligonucleotide populations which are resistant to nucleases and hydrolysis, modified oligonucleotides can be used and can include one or more substitute internucleotide linkages, altered sugars, altered bases, or combinations thereof. In one embodiment, oligonucleotides are provided in which the P(O)O group is replaced by P(O)S ("thioate"), P(S)S ("dithioate"), P(O)NR$_2$ ("amidate"), P(O)R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotide through an —O—, —N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). The use of 2-fluoro-ribonucleotide oligomer molecules can increase the sensitivity of a nucleic acid sensor molecule for a target molecule by ten-to-one hundred-fold over those generated using unsubstituted ribo- or deoxyribooligonucleotides (Pagratis, et al., Nat. Biotechnol. 15:68-73 (1997)), providing additional binding interactions with a target molecule and increasing the stability of the secondary structure(s) of the nucleic acid sensor molecule (Kraus, et al., Journal of Immunology 160:5209-5212 (1998); Pieken, et al., Science 253:314-317 (1991); Lin, et al., Nucl. Acids Res. 22:5529-5234 (1994); Jellinek, et al. Biochemistry 34:11363-11372 (1995); Pagratis, et al., Nat. Biotechnol 15:68-73 (1997)).

Nucleic acid aptamer molecules are generally selected in a 5 to 20 cycle procedure. In one embodiment, heterogeneity is introduced only in the initial selection stages and does not occur throughout the replicating process.

The starting library of DNA sequences is generated by automated chemical synthesis on a DNA synthesizer. This library of sequences is transcribed in vitro into RNA using T7 RNA polymerase and purified. In one example, the 5'-fixed: random:3'-fixed sequence is separated by a random sequence having 30 to 50 nucleotides.

Methods of Generating Regulated Aptamers

Selection methods for the isolation of aptamers that bind to a specific molecular target ('the target') only in the presence of a specific molecular effector ('the effector') are described.
Method (1): Selection From Naïve Sequence Pools Selection for ligand-regulated aptamers is performed with a nucleic acid pool containing 2'-fluoropyrimidines for additional serum stability. A DNA template with the sequence:

5'-GCCTGTTGTGAGCCTCCTGTCGAA-(N$_{40}$)-TTGAGCGTTTATTCTTGTCTCCCTAT-AGTGAGTCGTATTA-3' (SEQ ID NO:1) is synthesized using an ABI EXPEDITE™ DNA synthesizer, and purified by standard methods (N$_{40}$ denotes a random sequence of 40 nucleotides built uniquely into each aptamer). Approximately $10^{15}$ DNA molecules with unique sequences from the template pool can be PCR amplified using the primers YW.42.30.A (5'-TAATACGACTCACTATAGGGAGACAA-GAATAAACGCTCAA-3') (SEQ ID NO:2) and YW.42.30B (5'-GCCTGTTGTGAGCCTCCTGTCGAA-3') (SEQ ID NO:3). Amplified pool PCR product is precipitated with ethanol, re-suspended in water and desalted on a Nap-5 column (Pharmacia). Approximately $4 \times 10^{15}$ DNA molecules from the pool PCR amplification are transcribed in vitro using a mutant Y639F T7 RNA polymerase which accepts 2'-fluoropyrimidines (Sousa, 1999), 2'-fluoropyrimidine and 2'-OH purine NTPs, to yield ~$3 \times 10^{16}$ RNA molecules with corresponding sequences. Stabilized 2'-fluoro-pyrimidine pools made up of $10^{14}$-$10^{15}$ random sequences in a total volume of approximately 100 µl are contacted with either biotinylated target immobilized in neutravidin coated plates (Pierce) or adherent target-expressing cells immobilized in plates. A typical binding buffer used for the positive and negative selection steps contains 20 mM HEPES, pH 7.4, 150 mM NaCl, 10 mM MgCl2, 1 mM EDTA, 1 mM DTT, and 0.1 mg/ml tRNA (4 mM). Following a 10 min. negative incubation step at room temperature, RNAs which bind to the target alone will be removed in this negative selection step. The solution containing unbound RNA is then transferred to another identical well containing immobilized target and effector is added to the solution. The concentration of effector added can be adjusted to ultimately enrich molecules which respond to effector at the most appropriate concentration. Initially the effector is provided at saturating concentrations (typically millimolar for small molecule effectors such as glucose and high micromolar concentration for protein effectors) to ensure that molecules with any measure of effector dependence are isolated. In successive rounds of selection, the effector concentration can be reduced to preferentially isolate the most effector-dependent molecules. Following an equilibration period of 1 hour, wells are rinsed with excess binding buffer (typically washing four times with 120 ul of 1×ASB on a robotic plate washer with 30 sec. shakes). 50 µl of RT mix (RT primer, 4 µM; 5×"Thermo buffer", 1×; DTT, 100 mM; mixed dNTPs, 0.2 mM each; vanadate nucleotide inhibitor 200 µM; tRNA 10 µg/ml; 0.5 µl Invitrogen Thermoscript Reverse Transcriptase; brought to 50 µl with water) is added to the selection well and incubated at 65° C. for 30 min with tape over wells to reduce evaporation.

The RT reaction is diluted 10-fold into a 100 µl PCR reaction (containing 5'-primer, 1 µM; 3'-primer, 1 µM; 10×Invitrogen supplied PCR buffer (no Mg), lx; dNTPs, 0.2 mM each; MgCl$_2$, 3 mM; 1 ul Invitrogen Taq; 10 µl incubated RT reaction and brought to 100 µl with water) and thermocycled with the following schedule: 94° C., 1 min; 62° C., 1 min; 72° C. 3 min. The PCR reactions are assayed at 10 cycles by agarose gel, and then each successive 5 cycles until defined amplification bands are visible via ethidium bromide staining. Completed PCR reactions are purified using a Centri-sep column and diluted 10-fold into a 50 µl transcription reaction (4×TK Transcription buffer, 1×; $MgCl_2$, 25 mM; NTPs 5 mM each; NEB T7 RNA polymerase 2 ul; water to 50 µl). The transcription reaction is incubated overnight at 37° C. and the resulting transcription products are purified by denaturing polyacrylamide gel electrophoresis (10% gel).

The entire selection process is repeated until the fraction of molecules surviving both positive and negative selection increases significantly above the original naïve pool fraction, typically >10% of the input. Typically >10 cycles of selection are required for enrichment. Individual molecules within the enriched pool are isolated and characterized by subcloning the pooled template DNA using the TOPO TA cloning system (Invitrogen). Individual clones are sequenced and unique clones screened for effector dependent binding.

Method (2): Pre-Selection for Target Binding Followed by Effector-Dependent Selection.

Selection method (1) can be modified as follows if the probability that molecules with both target and effector binding properties exist in the starting pool is low. Instead of selecting initially for both target binding and effector dependence, in vitro selection can be used to isolate molecules with high affinity for the target. Following an optional diversification step (wherein the selected pool of target-binding sequences is partially randomized), effector-dependent selection can be applied. To isolate target specific aptamers, the previously described selection method is applied with the following modifications: (1) target is omitted from the negative selection step, and (2) effector is omitted from the positive selection step. 5-15 rounds of selection will typically yield a pool of target binding species containing 1-1000 unique sequences. Individual clones are screened for the ability to specifically bind to the target.

A diversified pool of sequences with increased likelihood of effector-dependent target binding activity can be generated by a number of means including the following:
(1) mutagenic PCR amplification of the enriched target-binding pool of sequences
(2) doped resynthesis of individual clone sequence(s) isolated from the target-binding pool, selecting clones that have high affinity and specificity binding. In this case, mutations are introduced at random across the sequence with 10-30% probability at each position or within specified regions of the sequence.
(3) resynthesis of a functionally important subdomain of individual clone sequence(s) isolated from the target-binding pool, flanked by random-sequence domains. Once individual aptamers are identified from the original pool, the minimal sequence element required for the biochemical activity can be identified through two parallel approaches: (1) truncation analysis by limited alkaline hydrolysis, and (2) doped reselection (methods are reviewed in Fitzwater & Polisky, 1996). In addition to helping to determine the minimal functional aptamer element, sequence variation introduced via doped reselection can provide mutants of the original clone with improved affinity or biochemical activity. The diversified pool is subjected to selection for effector-dependent target binding as described previously.

Method (3): Pre-Selection for Effector Binding Followed by Effector-Dependent Target Binding Selection.

Selection method (1) can be modified as follows if the probability that molecules with both target and effector binding properties exist in the starting pool is low. Instead of selecting initially for both target binding and effector dependence, in vitro selection can be used to isolate molecules with high affinity for the effector. Following an optional diversification step (wherein the selected pool of effector-binding sequences is partially randomized), effector-dependent, target-binding selection can be applied as described previously. To isolate effector-specific aptamers, the first selection method is applied with the following modifications: (1) target is omitted from the negative selection step, and (2) target is omitted from the positive selection step and instead effector is immobilized to the capture solid support. In the case of small molecule effectors such as glucose, conventional affinity chromatography using 200 µl agarose bead columns with 1-5 mM immobilized effector is the preferred immobilization format. 5-15 rounds of selection will typically yield a pool of effector binding species containing 1-1000 unique sequences. Individual clones are screened for the ability to specifically bind to the effector.

A sequence-diversified pool of effector-binding molecules can be generated by one of the following methods:
(1) mutagenic PCR amplification of the enriched effector-binding pool of sequences
(2) doped resynthesis of individual clone sequence(s) isolated from the effector-binding pool, selecting clones that have high affinity and specificity binding. In this case, mutations are introduced at random across the sequence with 10-30% probability at each position or within specified regions of the sequence.
(3) resynthesis of a functionally important subdomain of individual clone sequence(s) isolated from the effector-binding pool, flanked by random-sequence domains. The functionally important subdomain of the effector-binding sequences can be defined by truncation of the original clones, following by assays for effector binding.

The diversified pool is subjected to selection for effector-dependent target binding as described in selection method (1).

Method (4): Pre-Selection for Effector Binding and Target Binding Motifs, Followed by Effector-Dependent Target Binding Selection.

Selection method (1) can be modified as follows if the probability that molecules with both target and effector binding properties exist in the starting pool is low. Instead of selecting initially for both target binding and effector dependence, in vitro selection can be used to isolate two separate pools of molecules, one with high affinity for the effector and the other with high affinity for the target. Subdomains within the two pools can be engineered to create a chimeric pool of molecules in which each molecule contains one copy of an effector-binding motif and one copy of a target binding motif. This chimeric pool is then subjected to effector-dependent, target-binding selection as described previously.

To isolate target specific aptamers, selection method (1) is applied with the following modifications: (1) target is omitted from the negative selection step, and (2) effector is omitted from the positive selection step. To isolate effector-specific aptamers, the selection method (1) is applied with the following modifications: (1) target is omitted from the negative selection step, and (2) target is omitted from the positive selection step and instead effector is immobilized to the capture solid support. In the case of small molecule effectors such as glucose, conventional affinity chromatography using 200 µl agarose bead columns with 1-5 mM immobilized effector is the preferred immobilization format.

In the preferred embodiment, functional subdomains of high affinity clones from each of the target- and effector-specific pools are used to create the chimeric pool for effector-dependent selection. The functional subdomains can be identified as described previously (selection method (2)). The chimeric pool can be generated by linearly concatenating the functional motifs together with an intervening random sequence domain. Alternatively, the motifs can be combined at the secondary structure level by coupling via linking helices as described previously for effector-dependent ribozymes (Soukup, G., and Breaker, R. (1999) Design of allosteric hammerhead ribozymes activated by ligand-induced structure stabilization. Structure Fold Des 7 (7): 783-91).

Glucose-regulated aptamers with insulin-like bioactivity. Self-regulating aptamers that can functionally substitute for insulin can be created by the following method.

Step 1. Insulin-receptor (IR) binding activity. A pool of nucleic acid molecules is selected for the ability to bind to the extracellular portion of the insulin receptor using selection method (2). Previous studies have identified epitopes for IR-specific antibodies that are able to mimic the effect of insulin (Steele-Perkins, G, and Roth, R. A. (1990) Insulin-mimetic anti-insulin receptor monoclonal antibodies stimulate receptor kinase activity in intact cells. J. Biol. Chem. 265(16): 9458-9463). Protein fragments containing these epitopes are suitable starting points for the isolation of aptamers with insulin-mimetic activity. Modified monomeric and dimeric forms of IR-specific aptamers can be assayed for the ability to stimulate the intrinsic receptor kinase activity of IR and thus identify molecules with intrinsic agonist activities.

Step 2. Glucose regulation. The minimized functional domain of aptamers with insulin-like activity can be used to construct a pool of potentially glucose-dependent molecules by linear concatenation with a random sequence domain (e.g. $N_{20}$) and flanked by constant sequence primers to facilitate subsequent selection. Application of selection method (2) with high (e.g. 100 mM) initial concentrations of glucose as an effector yields glucose-regulator insulin-mimetic aptamers.

Pharmaceutical Compositions

The invention also includes pharmaceutical compositions containing regulated aptamer molecules. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

In practice, the compounds or their pharmaceutically acceptable salts, are administered in amounts which will be sufficient to induce lysis of a desired cell.

For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

The compounds of the invention can also be administered in such oral dosage forms as timed release and sustained release tablets or capsules, pills, powders, granules, elixers, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions. In particular, the materials of the present invention can be delivered to the ocular cavity with the methods described below. In addition, the materials of the present invention can be administered to subjects in the modalities known in the art as described below.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer-toxin and/or riboreporter molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the present invention range from 0.002 mg to 50 mg per kg of body weight per day.

Compounds of the present invention may be administered in a single daily dose, or the total daily dosage may be administered in divided doses of two, three or four times daily.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described above. All publications, patent applications, patents, and other references mentioned herein are incorporated by reference in their entirety. In the case of conflict, the present Specification, including definitions, will control. In addition, the materials, methods, and examples are illustrative only and not intended to be limiting.

EXAMPLE 1

Controlling Protein Activity with Ligand-Regulated RNA Aptamers

Confirmation of the invention described herein has been demonstrated by the work of another group described in Vuyisich et al. Chemistry and Biology, Vol. 9, 907-913, August 2002.

Controlling the activity of a protein is necessary for defining its function in vivo. RNA aptamers are capable of inhibiting proteins with high affinity and specificity, but this effect is not readily reversible. We describe a general method for discovering aptamers that bind and inhibit their target protein, but addition of a specific small molecule disrupts the protein-RNA complex. A SELEX protocol was used to raise RNA aptamers to the DNA repair enzyme, formamidopyrimidine glycosylase (Fpg), and neomycin was employed in each round to dissociate Fpg-bound RNAs. We identified an RNA molecule able to completely inhibit Fpg at 100 nM concentration. Importantly, Fpg activity is recovered by the addition of neomycin. We envision these ligand-regulated aptamers (LIRAs) as valuable tools in the study of biological phenomena in which the timing of molecular events is critical.

Controlling the activity of a protein is necessary for defining its function in vivo. RNA aptamers are capable of inhibiting proteins with high affinity and specificity, but this effect is not readily reversible. We describe a general method for discovering aptamers that bind and inhibit their target protein, but addition of a specific small molecule disrupts the protein-RNA complex. A SELEX protocol was used to raise RNA aptamers to the DNA repair enzyme, formamidopyrimidine glycosylase (Fpg), and neomycin was employed in each round to dissociate Fpg-bound RNAs. We identified an RNA molecule able to completely inhibit Fpg at 100 nM concentration. Importantly, Fpg activity is recovered by the addition of neomycin. We envision these ligand-regulated aptamers (LIRAs) as valuable tools in the study of biological phenomena in which the timing of molecular events is critical.

One potential drawback of the RNA aptamer approach described above is that once the aptamer is expressed in the cell and the target protein is inhibited, activity can no longer be precisely controlled. Tight temporal regulation of protein activity may be desired in certain instances when the timing of events is critical, such as during the cell cycle or in early development. (McCollum, D., and Gould, K. L. Trends Cell Biol. 11, 89-95 (2001); Ambros, V. Curr. Opin. Genet. Dev. 10, 428-433 (2000); Lee, R. C., and Ambros, V. Science 294, 862-864 (2001)). Having an expressed but nonfunctional (inhibited) gene product, then activating it at a desired point in time would be valuable in these cases. In such a system, one could monitor cellular activities or pathways while the target protein is inhibited, then activate the protein and detect changes.

Figure 2:
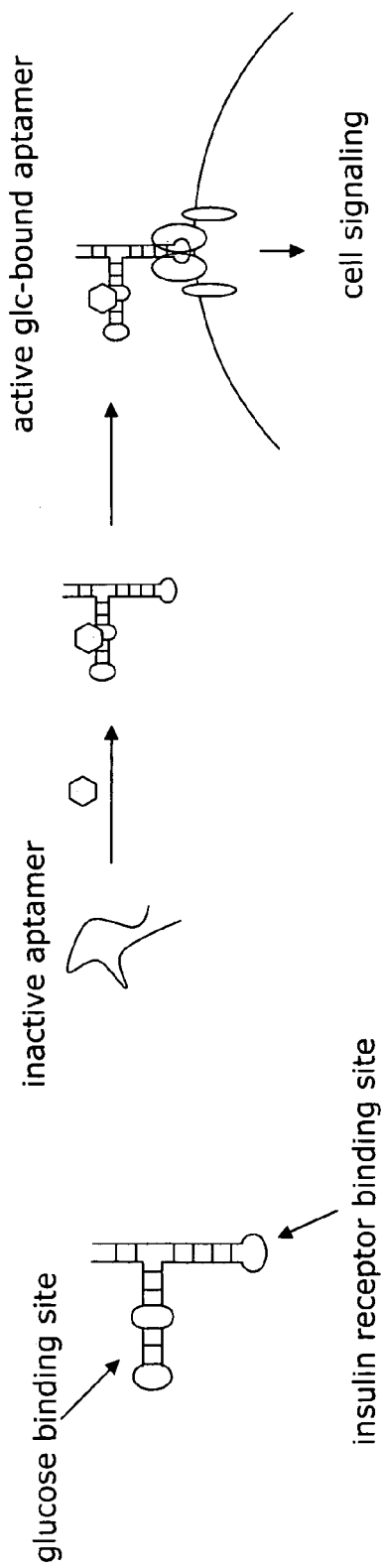
FIG. 2 shows a schematic of a glucose activated therapeutic to regulate insulin.

We reasoned that this goal might be accomplished with an RNA aptamer whose binding to the protein was itself regulated by an organic small molecule. Thus, a selected RNA could bind and inhibit the target protein. At a desired point in time, addition of the small molecule (inducer) would disrupt the RNA-protein complex, leading to the functional protein. (See FIG. 1, Vuyisich and Beal, Chem. & Biol. 9: 907-913 (2002)). Our approach was to employ a small molecule in an elution step during the SELEX protocol, leading to the amplification of RNAs that bind a target protein but dissociate from it in the presence of a small molecule. (See FIG. 2, Vuyisich and Beal, Chem. & Biol. 9: 907-913 (2002)). We refer to these RNAs as "ligand-regulated aptamers," or LIRAs. In systems that employ LIRAs, a functional protein can be inhibited for a specific period of time as the inhibition is temporally controlled by adding the inducer.

When considering the desired properties of a ligand regulated inhibitor, we realized that RNA structures should be capable of performing such tasks. In addition to aptamers' ability to bind a variety of proteins, in vitro selected RNAs are capable of recognizing small organic molecules with high affinity and specificity. (Wilson, D. S., and Szostak, J. W., Annu. Rev. Biochem. 66, 611-647 (1999); Hermann, T., and Patel, D. J., Science 287, 820-825 (2000); Jenison, R. D., et al., Science 263, 1425-1429 (1994)). Also, there are several examples of ribozymes whose activity can be regulated by the presence of small molecules called effectors. (Soukup, G. A., and Breaker, R. R., Proc Natl. Acad. Sci. USA 96, 3584-3589 (1999); Robertson, M. P., and Ellington, A. D., Nucleic Acids Res. 28, 1751-1759 (2000); Piganeau, N., et al., Angew Chem. Int. Ed. 39, 4369-4373 (2000); Hartig, J. S., et al., Nat. Biotechnol. 20, 717-722 (2002)). These effector-regulated ribozymes have been discovered using SELEX, where a fixed catalytic domain and a known small molecule binding domain are connected via a randomized RNA "communication module." Alternatively, the communication module and the catalytic domain can be fixed, and the small molecule binding domain can be randomized, thus selecting for new effector molecules. (Koizumi, M., et al., Nat. Struct. Biol. 6, 1062-1071 (1999)). In our approach, all parts of the LIRA are randomized, and we simultaneously select for an aptamer that can bind both the protein target and a small molecule.

For an Initial proof of principle experiment, we chose both a target protein and a potential inducer that are predisposed to bind nucleic acids. For the protein target, we employed the DNA repair enzyme formamidopyrimidine glycosylase (Fpg), also known as MutM. (Chestanga, C. J., and Lindahl, T. Nucleic Acids Res. 10, 3673-3684 (1979); Boiteux, S., et al., J. Biol. Chem. 265, 3916-3922 (1990)). This enzyme recognizes 8-oxo-dG lesions in DNA and removes the oxidized nucleotides from the strand, using its N-glycosylase and AP-lyase activities. (David, S. S., and Williams, S. D. Chem. Rev. 98, 1221-1261 (1998); Tchou, J., et al., Proc. Natl. Acad. Sci. USA 88, 4690-4694 (1991)). Our choice for the small molecule was neomycin, which belongs to the aminoglycoside class of antibiotics. These molecules have been shown to bind many naturally occurring RNA ligands. (Moazed, D., and Noller, H. F. Nature 327, 389-394 (1987); Yoshizawa, S., et al., Biochemistry 41, 6263-6270 (2002); Carter, A. P., et al. Nature 407, 340-348 (2000)). In addition, neomycin was used as a SELEX target and shown to bind a specific sequence motif in RNA. (Wallis, M. G., et al., Chem. Biol. 2, 543-552 (1995)).

Results

SELEX Results

Recombinant *E. coli* formamidopyrimidine glycosylase (Fpg) enzyme was selected as our initial protein target. (Chestanga, C. J., and Lindahl, T. Nucleic Acids Res. 10, 3673-3684 (1979); David, S. S., and Williams, S. D. Chem. Rev. 98, 1221-1261 (1998)). This nucleic acid binding protein is readily over-expressed, easily purified, and has a simple, well established assay for activity. (Boiteux, S., et al., J. Biol. Chem. 265, 3916-3922 (1990); Leipold, M. D., et al., Biochemistry 39, 14984-14992 (2000); Zharkov, D. O., et al., J. Biol. Chem. 272, 5335-5342 (1997)). A sequence-randomized RNA library was allowed to bind Fpg in solution followed by separation of free RNA from the Fpg-bound species using filter paper. In the first six rounds, a nonspecific urea buffer was used for elutions of Fpg-bound RNAs. In round seven, the RNA pool was split and used for two parallel selections. In the N selection, neomycin was used in the elution step. Therefore, only the RNAs that bound Fpg but dissociated in the presence of the aminoglycoside were collected and amplified. In the U selection, urea continued to be used in the elution step, selecting any RNA structure with affinity for Fpg.

During the N selection, the progress by round was measured by calculating the ratio of the amount of RNA eluted with 5 mM neomycin in the wash buffer and RNA eluted with wash buffer alone. This ratio climbed to near six in round 15. (See FIG. 3, Vuyisich and Beal, Chem. & Biol. 9: 907-913 (2002)). In round 18, the neomycin concentration was reduced to 1 mM in order to select for aptamers more sensitive to neomycin. The ratio dropped but quickly recovered. (See FIG. 3, Vuyisich and Beal, Chem. & Biol. 9: 907-913 (2002)). Finally, 200 μM neomycin was used in the last four rounds, after which the cDNA library was cloned, and the RNAs from this pool were designated N aptamers.

The U selection was performed for a total of 14 rounds, after which the library was tested for its ability to inhibit Fpg. Under single-turnover conditions, 1 μM library from the U selection after fourteen rounds completely inhibited the enzyme, whereas the same concentration of the initial RNA pool had no effect on Fpg. We cloned the cDNA pool at this stage and refer to the RNA clones from this selection as U aptamers.

We tested the ability of the RNA pool from the $23^{rd}$ N selection to inhibit Fpg in the presence of neomycin. As a control, we used the RNA pool from the fourteenth round of the U selection. The pool from the N selection was indeed more sensitive to neomycin (by an order of magnitude) than the U selection pool, which was never pressured to dissociate from Fpg in the presence of the aminoglycoside. After cloning, we tested 5 N and 9 U aptamers for their ability to inhibit Fpg with and without neomycin. In general, N aptamers were more sensitive to neomycin than U selection aptamers.

Aptamer Binding to Fpg

We tested several aptamers from each selection for their ability to bind and inhibit Fpg. Based on these results, we selected two clones (one from each selection) which bound Fpg with similar affinities and possessed similar inhibitory activities. We designated these the neomycin regulated aptamer (N1) and the control aptamer (U1). Using a quantitative filter binding assay, the $K_D$ was determined to be 7.5±1.6 nM for N1 and 2.7±0.9 nM for U1. Our steady-state experiments revealed complete inhibition of Fpg activity by both N1 and U1 aptamers at 100 nM concentration.

Effects of Neomycin on Aptamer Inhibition of Fpg

We wished to determine the relative response of the two selected aptamers to the presence of neomycin. Reaction components (aptamer, Fpg, and an aminoglycoside antibiotic) were incubated together, followed by the addition of labeled Fpg substrate under steady-state conditions. Full inhibition of the Fpg activity is observed with the N1 aptamer present at 100 nM concentration. (See FIG. 4B, lane 1, Vuyisich and Beal, Chem. & Biol. 9: 907-913 (2002)). As increasing concentrations of neomycin are added, the aptamer inhibition of Fpg is relieved (FIG. 4B, lanes 2-6, Vuyisich and Beal, Chem. & Biol. 9: 907-913 (2002)). At 100 μM neomycin, the Fpg activity approaches its maximum, in which ~2 nM product is observed (compare lanes 0 and 6, FIG. 4B, Vuyisich and Beal, Chem. & Biol. 9: 907-913 (2002)). The neomycin rescue was not observed when the control aptamer (U1), which binds Fpg with similar affinity as N1, was used to inhibit the enzyme. (FIG. 4C, Vuyisich and Beal, Chem. & Biol. 9: 907-913 (2002)). To determine if the disruption of the N1-Fpg complex is specific to neomycin, we repeated the experiment with the structurally similar aminoglycoside kanamycin. (FIG. 4F, Vuyisich and Beal, Chem. & Biol. 9: 907-913 (2002)). Importantly, this related aminoglycoside is unable to interfere with the inhibitory activity of the N1 aptamer under these conditions. (FIG. 4D, Vuyisich and Beal, Chem. & Biol. 9: 907-913 (2002)). The amount of product (nM) in FIGS. 4B-4D of Vuyisich and Beal, Chem. & Biol. 9: 907-913 (2002) was quantified and plotted as a function of aminoglycoside concentration. (FIG. 4E, Vuyisich and Beal, Chem. & Biol. 9: 907-913 (2002)).

Secondary Structure of the Neomycin-Regulated Aptamer

Sequencing of cDNA for the N1 aptamer allowed us to predict the RNA's secondary structure using the computer program MFOLD (http://bioinfo.math.rpi.edu/~mfold/ma/form1.cgi). (FIG. 5B, Vuyisich and Beal, Chem. & Biol. 9: 907-913 (2002); Mathews, D. H., et al., J. Mol. Biol. 288, 911-940 (1999)). To test the predicted model, we used ribonucleases specific for single-and double-stranded RNA, which included S1, V1, and T1. FIG. 5A of Vuyisich and Beal, Chem. & Biol. 9: 907-913 (2002) shows cleavage of N1 aptamer by S1 and V1 ribonucleases under native conditions. Major cleavage sites on the RNA are mapped onto the predicted secondary structure of the aptamer. (FIG. 5B, Vuyisich and Beal, Chem. & Biol. 9: 907-913 (2002)). The mapping also includes the major cleavage sites of T1 ribonuclease digest under native conditions, which are shown in FIG. 6A, lane 4 of Vuyisich and Beal, Chem. & Biol. 9: 907-913 (2002). In general, the reactivity observed with the different ribonucleases agrees with the predicted secondary structure.

Footprinting of Fpg and Neomycin on the Neomycin-Regulated Aptamer

In order to locate the binding sites for Fpg and neomycin on the N1 aptamer, cleavage protection assays (foot-printing) were performed. We utilized several ribonucleases (S1, V1, T1, and P1) for this purpose, and the results can be best demonstrated by ribonuclease T1 footprinting. (FIG. 6, Vuyisich and Beal, Chem. & Biol. 9: 907-913 (2002)). FIG. 6A of Vuyisich and Beal, Chem. & Biol. 9: 907-913 (2002) shows that cleavage by T1 diminishes at G27 as neomycin is added (lanes 5-13). Lanes 14-19 show a decrease in T1 cleavage from G27 to G35 in response to increasing amounts of Fpg. Thus, Fpg and neomycin bind the N1 aptamer at apparently overlapping sites at the junction between a stem structure and a single-stranded loop near the center of the RNA strand. (FIG. 6B, Vuyisich and Beal, Chem. & Biol. 9: 907-913 (2002)). When protection from T1 cleavage is converted to fraction RNA bound by neomycin, the data can be fitted using a single-site binding equation, which results in a $K_d$ of 0.94 ±0.06 µM. (FIG. 6C, Vuyisich and Beal, Chem. & Biol. 9: 907-913 (2002)).

The Importance of the 3' Stem-Loop of NI Aptamer

From the predicted secondary structure and the location of Fpg and neomycin binding sites on N1 aptamer, the 3' stem-loop of the RNA (nucleotides 60-91) appeared to be dispensable. To test this idea, we prepared two deletion mutants of the N1 aptamer, comprising 59 or 66 nucleotides from the 5' end. Neither of these RNAs was able to inhibit Fpg at 200 nM concentration. This result indicates that the 3' stem-loop is important for the inhibitory effect of N1, perhaps in maintaining the aptamer's three-dimensional structure.

Discussion

Several chemical genetics methods have been developed to delineate the functions of gene products that complement existing functional genetics approaches. (Specht, K. M., and Shokat, K. M, Curr. Opin Cell Biol. 14: 155-159 (2002); Verdugo, D. E., et al., Med. Chem. 44: 2683-2686 (2001); Shen, K., et al., J. Biol. Chem. 276, 47311-47319 (2001); McKenna, J. M., et al., J. Med. Chem. 45, 2173-2184 (2002); Norman, T. C., et al., J. Am. Chem. Soc. 118, 7430-7431 (1996); Kuruvilla, F. G., et al., Nature 416, 653-657 (2002); Belshaw, P. J., et al., Angew. Chem. Int. Ed. Engl. 34, 2129-2132 (1995); Famulok, M., et al., Chem. Biol. 8, 931-939 (2001)). One of these methods relies on the selection of an RNA aptamer inhibitor of the protein, which is then expressed inside the target cell. (Famulok, M., et al., Chem. Biol. 8, 931-939 (2001)). These RNA molecules are able to specifically block the function of a gene product. In this work, we build on this idea and present a method for temporally controlling the activity of a gene product which involves an RNA aptamer as the inhibitor of the target protein and a small molecule capable of relieving that inhibition (the inducer).

We utilized the SELEX method to evolve RNA aptamers that bind the DNA repair protein formamidopyrimidine glycosylase, Fpg. (Wilson, D. S., and Szostak, J. W., Annu. Rev. Biochem. 66, 611-647 (1999)). In addition, we introduced a step in the selection where RNA was eluted from filter-bound protein using the aminoglycoside antibiotic neomycin. This was the critical step that allowed us to collect and amplify only the RNA structures that satisfied two criteria: (i) the RNA must bind Fpg, and (2) the Fpg-bound RNA must dissociate from the protein in the presence of neomycin. After 23 rounds of SELEX and initial characterization of five clones, we further investigated the properties of clone N1, a 91-mer RNA aptamer. To ensure that the features of the N1 RNA were not arrived at by chance, we also performed a selection with Fpg using a highly stringent, nonspecific elution buffer (see Experimental Procedures). One of the clones from this selection (designated U1) bound Fpg with an affinity similar to that of N1 and was used for comparison to N1.

Although both N1 and U1 aptamers bind and inhibit Fpg similarly, the two aptamers showed dramatically different inhibitory activities in the presence of neomycin. (FIG. 4, Vuyisich and Beal, Chem. & Biol. 9: 907-913 (2002)). While most of the Fpg activity was rescued from inhibition by N1 in the presence of 100 µM neomycin the same concentration of the aminoglycoside had only a minimal effect on Fpg inhibition by the U1 aptamer. Furthermore, no appreciable rescue of Fpg activity was observed with 100 µM kanamycin, an aminoglycoside structurally related to neomycin. Thus, the ability of neomycin to rescue Fpg activity from the inhibitory effect of the N1 aptamer is dependent both on the structure of the evolved RNA aptamer and the small molecule used during the selection.

To shed light on the mechanism by which neomycin regulates the N1 aptamer, we carried out secondary structure prediction, structure probing studies, and foot-printing with this RNA. These experiments suggested a probable secondary structure as well as identified binding sites for Fpg and neomycin on the RNA. It is apparent that the selection carried out led to the isolation of an aptamer that had overlapping binding sites for Fpg and neomycin, suggesting the mode of action of neomycin is a competitive one. (FIG. 6, Vuyisich and Beal, Chem. & Biol. 9: 907-913 (2002)). Interestingly, the sequence at the neomycin binding site is similar to those previously implicated in binding aminoglycosides. For example, the 5'-GU-3' step, which is present in N1 aptamer as G27 and U28, has recently been shown to bind the aminoglycoside deoxystreptamine ring. (Yoshizawa, S., et al., Biochemistry 41, 6263-6270 (2002)). In addition, neomycin binding aptamers contain G-rich regions adjacent to a bulge, which is similar to the 5' end of N1 aptamer. (Wallis, M. G., et al., Chem. Biol. 2, 543-552 (1995)).

The method developed here for discovering a LIRA small molecule pair is potentially general for any target protein or protein domain. Such inhibitor/inducer pairs could be used to inhibit proteins in vivo, then relieve the inhibition at desired points in time. This would be valuable for the study of cellular phenomena in which the timing of molecular events is critical, such as in cell cycle regulation, circadian clocks, or controlling cell fates during early development. A system that includes neomycin as the inducer is probably not suitable for a cell biology application due to its toxicity. (Leach, B. E., et al., J. Am. Chem. Soc. 73, 2797-2800 (1951)). However, we believe this proof of principle exercise will pave the way for applications involving proteins whose roles are poorly understood and small molecules that are cell permeable and nontoxic. In the example reported here, we chose to use the presence of a small molecule as the switch in protein activity. In principle, other conditions could also have been chosen. For instance, an aptamer that dissociates from the target protein in the presence or absence of a specific metal ion or by a change in pH could lead to other means by which the target protein could be regulated. (Ellington, A. D., and Szostak, J. W. Nature 346, 818-822 (1990)). This could lead to a method to regulate protein activity only in certain cellular compartments or only in cells responding to a specific environmental stimulus.

In addition to these chemical genetic applications, the discovery of new protein-RNA complexes that are disrupted by small molecules will lead to a better understanding of the inhibition mechanisms possible. Indeed, as more LIRA/protein/small molecule combinations are discovered and structurally, kinetically, and thermodynamically characterized, an opportunity will exist to identify features of the protein-RNA complexes that make them susceptible to regulation by small molecules. This information will be valuable to those designing small molecule inhibitors of naturally occurring and functionally important protein-RNA complexes. (Hermann, T. Angew. Chem. Int. Ed. 39, 1890-1905 (2000)).

Significance

Several chemical genetics techniques have been developed that complement functional genetics in deciphering the cellular function of gene products. (Specht, K. M., and Shokat, K. M, Curr. Opin Cell Biol. 14: 155-159 (2002); Verdugo, D. E., et al., Med. Chem. 44: 2683-2686 (2001); Shen, K., et al., J. Biol. Chem. 276, 47311-47319 (2001); McKenna, J. M., et al., J. Med. Chem. 45, 2173-2184 (2002); Norman, T. C., et al., J. Am. Chem. Soc. 118, 7430-7431 (1996); Kuruvilla, F. G., et al., Nature 416, 653-657 (2002); Belshaw, P. J., et al., Angew. Chem. Int. Ed. Engl. 34, 2129-2132 (1995); Famulok, M., et al., Chem. Biol. 8, 931-939 (2001)). One of these approaches utilizes RNA aptamers that inhibit their target proteins in vivo. (Famulok, M., et al., Chem. Biol. 8, 931-939 (2001); Thomas, M., et al., J. Biol. Chem.272, 27980-27986 (1997)). We have extended the utility of this approach by demonstrating that RNA inhibitors of protein function can be discovered through in vitro evolution and are released from their targets in the presence of specific small molecules (inducers). This allows for greater temporal control of the targeted protein activity, as it can be reactivated upon addition of the inducer at a specific time point. This method should prove particularly useful in defining the function of gene products involved in phenomena where the timing of events is critical, such as the cell cycle, circadian clocks, or embryonic development. In addition, in-depth studies of ligand-regulated aptamers like those described here will identify features of protein-RNA complexes that make them susceptible to regulation by small molecules.

Experimental Procedures

General

Distilled, deionized water was used for all aqueous reactions and dilutions. Biochemical reagents were obtained from Sigma/Aldrich unless otherwise noted, Restriction enzymes and nucleic acid modifying enzymes were purchased from New England Biolabs. Oligonucleotides were prepared on a Perkin Elmer/ABI Model 392 DNA/RNA synthesizer with β-cyanoethyl phosphoramidites. 5'-Dimethoxytrityl protected 2'-deoxyadenosine, 2'-deoxyguanos1ne, 2'-deoxycytidine, and thymidine phosphoramidites were purchased from Perkin Elmer/AB1. (K-$^{32}$P]ATP (6000 Ci/mmol) and [$^{32}$P]pCp (3000 Ci/mmol) were obtained from DuPont NEN. Storage phosphor autoradiography was carried out using Imaging plates purchased from Kodak.

A Molecular Dynamics STORM 840 was used to obtain all data from phosphorimaging plates.

Fpg Purification

E. coli Fpg was overexpressed and purified as previously described. (Boiteux, S., et al., J. Biol. Chem. 265, 3916-3922 (1990); Leipold, M. D., et al., Biochemistry 39, 14984-14992 (2000); Zharkov, D. O., et al., J. Biol. Chem. 272, 5335-5342 (1997)). We estimated that the enzyme was 70% active.

Random Library Preparation

A 105 nt DNA oligonucleotide (0.2 nmol) was used as the template for a three-cycle PCR reaction, which yielded a 130 bp dsDNA product consisting of a T7 promoter and a 60-mer random region flanked by EcoRI and HindIII cloning sites. Transcription from this DNA generated a 105-nt-long random RNA pool. (Abelson, J. N. Methods Enzymol. 267, 291-335 (1996)).

Selections

In each round, ~2 nmol of RNA pool was denatured at 95° C. in 0.5 ml of the selection buffer (1×SB: 10 mM Tris-HCl, 50 mM NaCl, 2.5 mM $MgCl_2$ (pH 7.0]) and allowed to slowly cool to room temperature. A single 13 mm filter paper disc (HAWPO1300, Millipore) was added to the RNA pool, and the tube was gently mixed for 20 min. This step excluded filter paper binding RNAs. The RNA pool was then transferred to a tube with 0.3 nmol of Fpg and allowed to bind for 20 min with gentle mixing. To separate Fpg.bound from free RNA, a vacuum manifold-mounted 96-well plate with filter paper bottoms (MAVMO96OR and MAHAS4510, Millipore) was used. The binding reaction was loaded into a well, and vacuum was applied for 1 min. Unbound RNAs passed through the filter, while Fpg and the bound RNAs were retained. The RNA-protein complexes were washed with 1 ml of 1×SB to remove weakly binding RNAs. In the first six rounds, the Fpg-bound RNAs were eluted with 0.2 ml of urea elution buffer (100 mM Na citrate, 7 M urea, 10 mM EDTA [pH 5.2]) which was preheated to 65° C. The eluted RNAs were washed three times with 0.5 ml water in a YM-10 microcon concentrator (Millipore), then treated with 5 units of RNase-free DNase I (Promega) for 3 hr at 37° C. Access RT-PCR kit (Promega) was used to amplify RNA winners from each round. After six rounds, the RNA pool was divided and used for two parallel selections. One selection utilized the same urea elution step as before and was performed for an additional eight rounds. The other selection employed elution buffer that consisted of 1×SB supplied with neomycin. The number of rounds in this selection (including the initial six rounds) was 23.

Cloning

The cDNA from final rounds of each selection was digested with EcoRI and HindIII (NEB), then cloned into pUC-19 vector and transformed into E. coli XL-1 Blue cells. Plasmids coding for individual RNA clones were isolated, sequenced, and used for production of aptamers. (Sambrook, J., et al., Molecular Cloning: A Laboratory Manual (Cold Spring Harbor, N.Y.; Cold Spring Harbor Laboratory Press) (1989)).

Filter Binding Assays

Protein-RNA binding affinity was assessed using filter binding assays. These were carried out by mixing increasing concentrations of Fpg with small amounts (0.1 nM) of 5' end-labeled aptamer, followed by incubation for 15 min at room temperature. Bound and free RNA were separated using filter paper under vacuum filtration and washing. Both the total and free (flow-through plus the wash) RNA were measured by scintillation counter, and fraction bound was calculated. The data were plotted as a function of Fpg concentration and fitted using a single-site binding equation:

fraction bound=$[Fpg]/([Fpg]+K_d)$.

Fpg Assays

Fpg activity assays were carried out at room temperature in 1×SB under steady-state conditions with 1 nM Fpg. An 18-mer dsDNA was used as the Fpg substrate. The 8-oxo-dG-containing strand was 5' labeled and had the following sequence; d(5'-TCATGG GTC(8-oxo-G)TCGGTATA-3') (SEQ ID NO:4), and the complementary strand contained a cytidine opposite 8-oxo-dG. Reaction components were mixed in 18 μl and incubated for 12 min, followed by the addition of 2 μl of 200 nM DNA substrate (20 nM final). After 7 min, reactions were quenched with 15 μl of 95° C. stop solution (97% formamide, 0.02% xylene cyanol in 0.2×TBE) and heated at 95° C. for an additional 5 mm. The reactions were resolved on 15%, denaturing PAGE and visualized using phosphorimager screens. The amount of product was calculated as a percent of 20 nM substrate and without any inhibitors was measured to be approximately 2 nM under these conditions.

Secondary Structure Prediction and Testing

Secondary structure prediction was performed using the web-based MFOLD program on Dr. Michael Zuker's website, http://bioinfo.math.rpi.edu/~mfold/ma/form1.cgi. (Mathews, D. H., et al., J. Mol. Biol. 288, 911-940 (1999)). Testing of the predicted structure was carried out using T1, S1, and V1 ribonuclease digests. All reactions were carried out for 10 min at room temperature in 1×SB under native conditions and in the presence of 10 μg/mL of yeast tRNA Phe. In the case of S1 ribonuclease, reactions were supplied with 0.1 mM $ZnCl_2$ for optimal activity.

T1 Quantitative Footprinting

Footprints for both Fpg and neomycin were obtained using T1 RNase under native conditions. The reactions were performed in 1×SB at room temperature with 10 μg/ml of $tRNA^{Phe}$. Increasing amounts of Fpg or neomycin were incubated with 10 nM labeled aptamer for 10 min, followed by a 10 min enzyme digest. The reactions were quenched with 15 μl of stop solution, heat denatured, and 5 pl of each was resolved on 10% denaturing PAGE. After phosphorimaging the gel, the cleavage efficiency at G27 was calculated by subtracting the background band in the control lane and normalizing for the different loading per lane. The cleavage data were converted into binding data for neomycin, assuming that the maximum cleavage corresponds to 0% occupancy by neomycin and that the minimum cleavage corresponds to 100% occupancy by neomycin. Fraction of aptamer bound by neomycin was plotted as a function of neomycin concentration, and the data were fitted using a single-site binding equation:

fraction bound=$[neo]/([neo]+K_d)$.

The results are reported as the average and standard deviation for three different experiments.

EXAMPLE 2

Glucose Regulated Aptamers

Glucose causes an insulin receptor agonist aptamer to become activated, binding the insulin receptor target and triggering glucose uptake by cells.

A method of preparing a glucose regulated aptamer includes the following steps: 1) separately isolate aptamers with insulin receptor agonist activity and glucose binding activity using SELEX, 2) engineer a diverse sequence pool of molecules that contains both functional motifs, and 3) select for aptamers whose receptor binding activity is dependent upon the presence of glucose.

Alternatively, a pool of nucleic acid molecules is selected for the ability to bind to the extracellular portion of the insulin receptor using selection method (2). Previous studies have identified epitopes for IR-specific antibodies that are able to mimic the effect of insulin (Steele-Perkins, 1990). Protein fragments containing these epitopes are suitable starting points for the isolation of aptamers with insulin-mimetic activity. Modified monomeric and dimeric forms of IR-specific aptamers can be assayed for the ability to stimulate the intrinsic receptor kinase activity of IR and thus identify molecules with intrinsic agonist activities.

The minimized functional domain of aptamers with insulin-like activity can be used to construct a pool of potentially glucose-dependent molecules by linear concatenation with a random sequence domain (e.g. $N_{20}$) and flanked by constant sequence primers to facilitate subsequent selection. Application of selection method (2) with high (e.g. 100 mM) initial concentrations of glucose as an effector yields glucose-regulator insulin-mimetic aptamers.

The invention having been described by way of illustration by the non-limiting examples is now defined by the spirit and scope of the following claims.

What is claimed is:

1. A method for selecting a regulated aptamer comprising the steps of:
   a) identifying a first pool of candidate aptamers comprising a first binding domain that binds to a first ligand, wherein the first ligand is selected from the group consisting of a small molecule, a peptide, a protein and a saccharide, and a second pool of candidate aptamers comprising a second binding domain that binds to a second ligand, wherein the second ligand is a protein or a peptide;
   b) engineering a chimeric pool of aptamers wherein individual aptamers within the chimeric pool comprise a first binding domain of a candidate aptamer from the first candidate pool linked to a second binding domain of a candidate aptamer from the second candidate pool; and
   c) selecting, using SELEX, an aptamer from the chimeric pool wherein binding of the second ligand by the second binding domain of the selected aptamer is activated by binding of the first ligand by the first binding domain, and wherein binding of the second ligand by the second binding domain modulates a biological activity of the second ligand.

2. The method of claim 1, wherein the identifying step further comprises using SELEX to isolate the first pool of candidate aptamers.

3. The method of claim 1, wherein the identifying step further comprises using SELEX to isolate the second pool of candidate aptamers.

4. The method of claim 1, wherein the selecting step further comprises contacting the chimeric pool of aptamers with the second ligand, in a negative selection step, to result in a bound ligand and unbound ligand mixture, and partitioning the unbound ligand mixture; contacting only the unbound ligand mixture, in a positive selection step, with the first and second ligands to result in a second bound ligand mixture and unbound ligand mixture; and selecting an aptamer from the second bound ligand mixture.

5. The method of claim 4, wherein the selecting step further comprises amplifying and contacting the second bound ligand mixture with the second ligand in the negative selection step and repeating the negative and positive selection steps iteratively prior to selecting the aptamer.

6. The method of claim 1, wherein the engineering step comprises linking the first and second binding domains of the first and second candidate aptamers by linearly concatenating the first and second ligand binding domains with an intervening random sequence domain.

7. The method of claim 1, wherein the engineering step comprises linking the first and second binding domains of the first and second candidate aptamers by coupling the first and second binding domains with linking helices.

8. The method of claim 1, wherein the first ligand is a protein selected from the group consisting of a growth factor, a transcription factor, an enzyme, an immunoglobulin, a receptor and a hormone.

* * * * *

SEQUENCE LISTING

<160> NUMBER OF SEQ ID NOS: 4

<210> SEQ ID NO 1
<211> LENGTH: 104
<212> TYPE: DNA
<213> ORGANISM: Artificial Sequence
<220> FEATURE:
<223> OTHER INFORMATION: Description of Artificial Sequence:Aptamer DNA
      Template
<220> FEATURE:

```
<221> NAME/KEY: misc_feature
<222> LOCATION: (25)..(64)
<223> OTHER INFORMATION: Wherein n is a or t or c or g.

<400> SEQUENCE: 1
gcctgttgtg agcctcctgt cgaannnnnn nnnnnnnnnn nnnnnnnnnn nnnnnnnnnn      60
nnnnttgagc gtttattctt gtctccctat agtgagtcgt atta                      104

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:Aptamer
      Template Primer YW.42.30.A

<400> SEQUENCE: 2
taatacgact cactataggg agacaagaat aaacgctcaa                           40

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Aptamer
      Template Primer YW.42.30.B

<400> SEQUENCE: 3
gcctgttgtg agcctcctgt cgaa                                            24

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:FPG
      Substrate
<220> FEATURE:
<221> NAME/KEY: misc_feature
<222> LOCATION: (10)
<223> OTHER INFORMATION: wherein n is 8-oxo-dG

<400> SEQUENCE: 4
tcatgggtcn tcggtata                                                   18
```